(12) United States Patent
Janssen

(10) Patent No.: US 10,690,550 B2
(45) Date of Patent: Jun. 23, 2020

(54) METHOD FOR MONITORING A LINE FOR UNCHANGED AMBIENT CONDITIONS AND MEASURING ARRANGEMENT FOR MONITORING A LINE FOR CHANGED AMBIENT CONDITIONS

(71) Applicant: LEONI KABEL GMBH, Nuremberg (DE)

(72) Inventor: Bernd Janssen, Friesoythe (DE)

(73) Assignee: LEONI Kabel GmbH, Nuremberg (DE)

( * ) Notice: Subject to any disclaimer, the term of this patent is extended or adjusted under 35 U.S.C. 154(b) by 301 days.

(21) Appl. No.: 15/677,199

(22) Filed: Aug. 15, 2017

(65) Prior Publication Data

US 2018/0045578 A1    Feb. 15, 2018

(30) Foreign Application Priority Data

Aug. 15, 2016   (DE) .......................... 10 2016 215 173

(51) Int. Cl.
   *G01K 1/16*    (2006.01)
   *G01K 7/34*    (2006.01)
   (Continued)

(52) U.S. Cl.
   CPC .................. *G01K 1/16* (2013.01); *G01K 7/00* (2013.01); *G01K 7/16* (2013.01); *G01K 7/343* (2013.01);
   (Continued)

(58) Field of Classification Search
   CPC .. G01N 21/8806; G01N 27/3274; G01K 7/16; G01J 5/0096; G01J 5/02
   (Continued)

(56) References Cited

U.S. PATENT DOCUMENTS 4,140,393 A * 2/1979 Cetas ..................... G01K 11/00
                                                    250/474.1
4,724,439 A * 2/1988 Wiley .................. G01K 11/006
                                                      342/351
(Continued)

FOREIGN PATENT DOCUMENTS

DE      19516436 C1 *  8/1996  ............... G01K 7/16
DE      69417360 T2     7/1999
(Continued)

OTHER PUBLICATIONS

Hiebel, Michael: "Grundlagen der vektoriellen Netzwerkanalyse". Rohde & Schwarz.

*Primary Examiner* — Gail Kaplan Verbitsky
(74) *Attorney, Agent, or Firm* — Laurence A. Greenberg; Werner H. Stemer; Ralph E. Locher

(57) ABSTRACT

A method monitors a line for changed ambient conditions. The line has a measuring line with a predetermined length and a measuring conductor surrounded by insulation having a known dielectric constant. In the method, an analog signal having a predetermined frequency is generated, the signal is divided into a reference signal and an operating signal, the operating signal is fed into the measuring conductor, a return signal obtained from the operating signal is combined with the reference signal and by a phase shift between the reference signal and the return signal, a measure is determined for the changed condition, particularly for a temperature change.

8 Claims, 2 Drawing Sheets

(51) Int. Cl.
  *G01K 7/16*   (2006.01)
  *G01R 31/58*  (2020.01)
  *G01K 7/00*   (2006.01)
  *G01N 25/48*  (2006.01)
  *G01N 33/38*  (2006.01)
  *G01R 31/50*  (2020.01)

(52) U.S. Cl.
  CPC ....... *G01N 25/4853* (2013.01); *G01N 33/383* (2013.01); *G01R 31/58* (2020.01); *G01K 2007/166* (2013.01); *G01K 2205/00* (2013.01); *G01R 31/50* (2020.01)

(58) Field of Classification Search
  USPC ...................................................... 356/43, 44
  See application file for complete search history.

(56) References Cited

U.S. PATENT DOCUMENTS

| | | | |
|---|---|---|---|
| 4,868,506 A | 9/1989 | DiStefano et al. | |
| 5,051,595 A * | 9/1991 | Kern | A62C 3/0271 |
| | | | 250/227.14 |
| 5,151,869 A * | 9/1992 | Alcala | G01N 21/6408 |
| | | | 250/458.1 |
| 5,228,780 A * | 7/1993 | Shepard | G01K 7/30 |
| | | | 374/175 |
| 5,655,840 A | 8/1997 | Powell | |
| 5,688,050 A * | 11/1997 | Sterzer | A61B 5/015 |
| | | | 374/121 |
| 5,721,615 A * | 2/1998 | McBride | G01D 5/35303 |
| | | | 356/477 |
| 5,928,222 A * | 7/1999 | Kleinerman | G01J 5/08 |
| | | | 374/E11.017 |
| 6,380,534 B1 * | 4/2002 | Farhadiroushan | |
| | | | G01D 5/35364 |
| | | | 250/227.14 |
| 6,535,824 B1 * | 3/2003 | Mansky | B01J 19/0046 |
| | | | 374/49 |
| 6,905,242 B2 * | 6/2005 | Heuer | G01F 1/6986 |
| | | | 374/142 |
| 7,915,994 B2 * | 3/2011 | Habboosh | G01K 1/10 |
| | | | 338/22 R |
| 8,057,094 B2 * | 11/2011 | Luniewski | H01L 23/34 |
| | | | 257/467 |
| 8,739,621 B2 * | 6/2014 | Kaercher | G01F 23/22 |
| | | | 73/295 |
| 2003/0099574 A1 * | 5/2003 | Bentsen | G01N 21/6408 |
| | | | 422/82.07 |
| 2006/0153274 A1 * | 7/2006 | Seebacher | G01K 11/32 |
| | | | 374/130 |
| 2011/0102183 A1 | 5/2011 | Tenchio | |
| 2011/0235675 A1 * | 9/2011 | Matsudo | H01L 21/67109 |
| | | | 374/130 |
| 2015/0168253 A1 | 6/2015 | Chin et al. | |
| 2015/0268078 A1 * | 9/2015 | Zhang | G01F 1/6884 |
| | | | 374/45 |
| 2016/0290876 A1 | 10/2016 | Koeppendoerfer et al. | |
| 2019/0033453 A1 * | 1/2019 | Crouch | G01S 17/102 |

FOREIGN PATENT DOCUMENTS

| | | | | |
|---|---|---|---|---|
| DE | 102007008263 A1 | 8/2008 | | |
| DE | 102013227051 A1 | 6/2015 | | |
| FR | 2936318 A1 * | 3/2010 | ............... | G01K 7/42 |
| GB | 2447122 A | 9/2008 | | |
| JP | H0712864 A | 1/1995 | | |
| SU | 1364965 A * | 1/1985 | | |
| WO | 2009115127 A1 | 9/2009 | | |
| WO | 2015091552 A1 | 6/2015 | | |

* cited by examiner

METHOD FOR MONITORING A LINE FOR UNCHANGED AMBIENT CONDITIONS AND MEASURING ARRANGEMENT FOR MONITORING A LINE FOR CHANGED AMBIENT CONDITIONS

CROSS-REFERENCE TO RELATED APPLICATION

This application claims the benefit, under 35 U.S.C. § 119, of German patent application DE 10 2016 215 173.8, filed Aug. 15, 2016; the prior application is herewith incorporated by reference in its entirety.

BACKGROUND OF THE INVENTION

Field of the Invention

The invention relates to a method and to a measuring arrangement for monitoring a line for changed ambient conditions.

In this context, the line is an electrical line having at least one conductor which is surrounded by insulation. The conductor surrounded by insulation will also be called core in the text which follows. The insulation has a predetermined dielectric constant. A signal transmission within the electrical conductor is influenced by the dielectric constant.

Frequently, a number of cores are combined to form one line. In many applications, for example in the automotive field, lines are then subject to the most varied loadings which are frequently unknown with respect to their duration and intensity. Even basically diverse and very changeable ambient conditions, particularly heat effects, can often not or not sufficiently be estimated for being able to predict wear of a line. To be able to guarantee a particular minimum life, a line is typically configured to be excessively dimensioned.

SUMMARY OF THE INVENTION

On the basis of this, the invention is based on the object of providing for a simple and cost-effective monitoring of a line for changed ambient conditions.

The method according to the invention is used for monitoring a line for changed ambient conditions. The line has a measuring line having a predetermined length which has a measuring conductor surrounded by an insulation having known dielectric constant. In this context, the line can have other line components, particularly other electrical line cores or other electrical lines, apart from the measuring line. In a preferred variant of the embodiment, the line only has the measuring line, however.

In the method an analog signal having a defined frequency is also generated. This signal is subsequently divided into a reference signal and an operating signal, the operating signal subsequently being fed into the measuring conductor for the dividing. The signal coupled into the measuring conductor passes through the measuring conductor preferably twice, i.e. passes through a forward path and a reverse path. The signal propagating in the return path, subsequently called return signal, is subsequently combined with the previously separated reference signal. By a phase shift between the reference signal and the return signal, a measure is finally determined for the changed ambient condition. The return signal is presently considered as a part of the operating signal which is propagating on the return path.

This ambient condition or also ambient parameter is particularly the temperature. The term ambient condition or ambient parameter is to be understood as a general term in this context. According to a first variant of the embodiment, it is an ambient condition outside the line. In this case, a further component is, therefore, monitored generally with the aid of the measuring line. Alternatively, the condition is an internal ambient condition, for example a condition of the line itself, for example the temperature of the line. In the latter case, in which it is thus a matter of an inherent internal condition of the line which is monitored, the monitoring method is, therefore, used for monitoring the line itself. By means of the values determined for the changed inherent condition, prognoses are also preferably derived for the wear of the line.

The method proposed here is basically based on the consideration that an operating time of the signal fed into the measuring conductor depends, in particular, on the dielectric constant. This, in turn, varies with the ambient conditions, particularly the temperature. A changing in ambient temperature, therefore, effects the run time of the signal to be expected via the dielectric constant. Since the measuring conductor has a predetermined defined length, a changed dielectric constant leads to a changed (electrical) path length for the signal.

By superimposing the return signal with the reference signal and the different temperature-dependent run times, the changed (ambient) condition, particularly the changing temperature, can lastly be inferred from the phase shift between reference signal and the return signal resulting from the different run times. Appropriately, an absolute current temperature is inferred by a corresponding calibration.

The use of an analog signal is of particular significance for the present method. This is generally considered to be a stepless signal having a continuous signal profile without interruptions, in distinction from a digital signal which typically only has a step sequence of (two) discrete states (0, 1). This has the advantage that this has a distinctly lower frequency in comparison with digital measuring pulses. This leads to the signal attenuation of the operating signal being comparatively low.

In a preferred embodiment, the reference signal and the return signal are superimposed to form a resultant signal and from the amplitude of the resulting signal, the measure is then determined for the changing condition. The resulting signal is therefore the sum or difference signal formed from reference and return signal. From the sum or difference value of the amplitude, the phase relation between the two signals and thus, in turn, the dielectric constant changed due to temperature and thus lastly the changed temperature is inferred—with known starting amplitude of the reference signal and of the return signal.

The signal is generally a periodic signal having a predetermined frequency, particularly a continuously changing signal having a steadily rising or falling amplitude, especially a sinusoidal or cosinusoidal signal. In addition, there is also the option, in principle, to use other signal geometries such as, for example triangular signals.

Under predetermined normal conditions, for example, therefore, at a normal ambient temperature of, for example, 20° C., the return signal preferably has a run time to be expected. The frequency of the signal and thus also the frequency of the operating signal coupled into the measuring conductor is then selected and tuned in such a manner that at the assembly point, at which the return signal and the reference signal are brought together, especially added, a predetermined defined phase difference occurs. For such normal conditions, a phase difference of 90° or 270° is preferably set. By means of this measure, changes in state, particularly temperature changes, can be readily detected. Especially, for example, both temperature increases and temperature decreases can be reliably detected and distinguished. When the two signals are combined, they are, in particular, added, i.e. their amplitudes are vectorially added. With a phase offset of 0°, a maximum is obtained and with a phase offset of 180°, a minimum.

To provide for as unambiguous a statement as possible about the ambient condition, it is then also provided that the frequency is selected in such a manner that a phase shift between the reference signal and the return signal is 180° in amount, i.e. the maximum phase shift to be expected for a predetermined maximum measuring range (temperature range) is 180°. Preferably, a maximum phase shift to be expected is set to less than or equal to +/45°. The maximum phase shift is thus predetermined and is selected in such a manner that it correlates with a maximum run time difference to be expected. The maximum run time difference to be expected is then determined by the maximum change in the (ambient) condition to be expected. Therefore, a maximum monitoring range is virtually predetermined for the parameter to be monitored (ambient condition). Taking into consideration this maximum monitoring range and the defined length of the measuring conductor, the maximum expected run time difference between the run times at maximum and minimum value of the ambient condition is firstly determined in advance. This run time difference is thus to be expected for the return signal within the predefined maximum range of values for the variation of the (ambient) parameter. From the maximum run time difference thus determined and a predetermined maximum phase shift, the frequency of the signal is then derived and set.

Appropriately, the frequency is then within the range of several 10 kHz up to a maximum of several 10 MHz. The frequency is preferably overall within the range of between 0.5 and 60 MHz and preferably at 30 MHz. In this context, the predefined frequency decreases with increasing line length. This dependence of the frequency on the line length is of particular advantage since a signal attenuation usually increases at higher frequencies which thus may have negative consequences in certain circumstances in the case of longer measuring conductors. Due to the reciprocal relation between line length of the measuring conductor and frequency, the present method with the analog measuring signals is, therefore, particularly suitable at greater line lengths.

The line lengths of the measuring conductor are generally preferably within the range of some meters to some 10 m. In principle, the length of the measuring conductor is not restricted, however. The length of the measuring conductor can also be several 10 m up to 100 m or some 100 m.

For the evaluation of the superimposed resulting signal, which is obtained by forming sums or difference, it is also of special significance that the amplitude of the return signal is known. This is suitably determined in advance for example computationally or also by reference measurements, and taken into consideration correspondingly in the evaluation.

If only a small amplitude of the return signal is to be expected because of for example particularly large line lengths or other influences, then the return signal is amplified in accordance with a preferred embodiment, for example in such a manner that it has at least approximately the same amplitude as the reference signal.

The measuring conductor or the measuring line, respectively, is preferably generally a spur line, that is to say a line which is passed twice by the operating signal, i.e. on a forward path and on a return path.

According to a first variant of the embodiment, the return signal is then suitably a reflected component of the operating signal. In this variant of the embodiment, the measuring conductor is open at its end, that is to say electrically contactless and, for example, not connected to a predetermined potential. At such an open end, a reflection of the signal takes place in a manner known per se. Alternatively, the end is short circuited to ground which corresponds to an additional phase shift of 180°. In these variants of the embodiment, the reflected components of the operating signal are called the return signal.

Especially in this variant of the embodiment, the return signal is suitably coupled into a return conductor separate from the measuring conductor. For this purpose, a so-called directional coupler is preferably used. In a simplest variant of the embodiment, the return conductor is simply arranged adjacently to the measuring conductor and the return signal is coupled in by the effect of crosstalk. Especially in this variant of the embodiment, in which the return signal is thus coupled into a return conductor separate from the measuring conductor, an amplification of the return signal coupled into the return conductor is provided before the return signal provided via the return conductor is combined with the reference signal.

According to an alternative, particularly preferred embodiment, the measuring line has two cores or conductors which are connected to one another, i.e. short circuited. The measuring line is again preferably a spur line, the two cores then being connected to one another at their ends. The forward path of the measuring line is then formed by one core and the return path of the measuring line is formed by the other core. In this case, the return signal is, therefore, not mandatorily a reflected signal but directly the operating signal propagating via the return path, i.e. via the second core.

In this arrangement, the measuring line suitably has a third conductor which is, in particular, formed by a shielding and, in particular, is connected to a reference potential, for example ground. A return path is virtually formed thereby for the alternating voltage signal. In this case the measuring line is therefore preferably overall a two-core shielded line in which the two cores are short circuited to one another at their ends.

According to a third and simplest variant, finally, the measuring line is connected on one side to the transmitter and with the other side directly to the receiver. For this purpose, a two-wire line or a coaxial line also, for example, is connected to a feeding side and to a receiver side. Here, too, the return signal is, in particular, the operating signals propagating in the measuring conductor 24 which is then compared with the reference signal RS.

According to the invention, the object is also achieved by a measuring arrangement which, in particular is configured for carrying out the method described before. This measuring arrangement has the following components:

a) a measuring line having a predetermined length which has a measuring conductor which is surrounded by an insulation which has a temperature-dependent dielectric constant,
b) a signal generator for generating an analog signal having a predetermined frequency,
c) a splitter for generating a reference signal and from the operating signal or from the analog signal,
d) the measuring conductor being connected to an output of the splitter for coupling the operating signal into the measuring conductor, and e) an evaluating unit for determining a measure for the changed condition on the basis of a phase offset between the reference signal and the return signal.

In this context, the evaluating unit suitably has a summing or a differentiating element which is configured for superimposing the return signal with the reference signal. In particular, this is for example a differential amplifier. The resultant signal obtained from it is then preferably supplied to a voltage meter by which the amplitude of the resultant signal is determined.

In this context, all feeding and evaluating components of the measuring arrangement are preferably integrated in a common monitoring unit. At this monitoring unit which is thus a constructional unit and, for this purpose, is arranged, for example, in a common housing or on a common carrier, such as, for example, a board, only the measuring line is connected. This is especially done via a reversible connection option at contact terminals.

The measuring line itself is then still run in a component to be monitored, particularly for monitoring the temperature within the component.

According to a first embodiment, the component in this case is a cable which is to be monitored itself. The measuring line is therefore integrated inside an electrical cable. Apart from temperature monitoring, the cable can generally also be checked for other conditions, particularly mechanical loads, especially when these have led to a break of the measuring conductor.

The cable is, in particular, in this context, a cable which is run, when applied, in a motor vehicle, for example in the engine area etc. Such a cable has typically a length of only a few meters up to maximum of 10 m.

According to a second variant of the embodiment, the component to be monitored is a component such as, for example, an engine component or another component, the temperature of which is to be monitored and/or controlled.

According to a particularly preferred embodiment, the component is a compound, the compound changing by exothermic or endothermic reaction. Via the measuring arrangement, there is therefore the advantageous possibility of monitoring the exothermic or endothermic reaction. The compound is, especially, a curable or dryable compound, especially, for example, a casting compound, especially in the construction industry. This compound is especially concrete. By means of the temperature, it is possible to reliably infer the degree of drying or hardening of the concrete also in its interior. The measuring line is therefore embedded in the compound and remains in it after the hardening of the compound.

Other features which are considered as characteristic for the invention are set forth in the appended claims.

Although the invention is illustrated and described herein as embodied in a method for monitoring a line for unchanged ambient conditions and a measuring arrangement for monitoring a line for changed ambient conditions, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
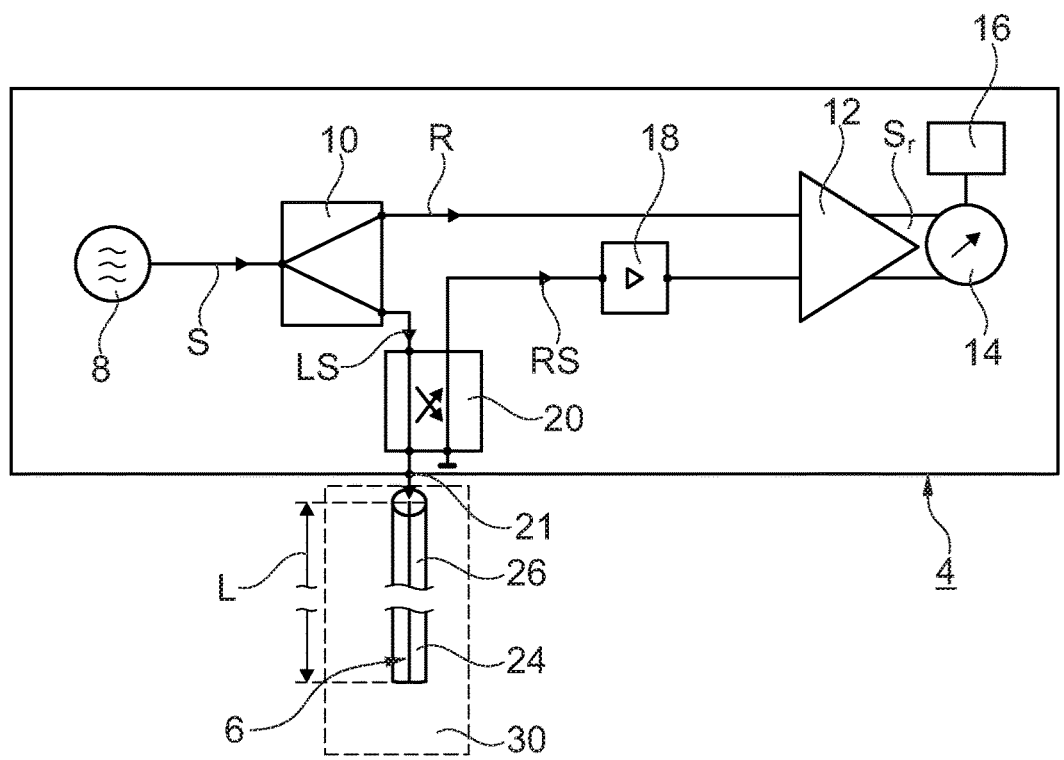
FIG. 1 is a schematic diagram showing a first variant of the embodiment of a measuring arrangement according to the invention.

In the figures, identically acting parts are provided in each case with the same reference numerals.

Referring now to the figures of the drawings in detail and first, particularly to FIG. 1 thereof, there is shown a measuring arrangement 2 which has a monitoring unit 4, to which a measuring line 6 is connected. The monitoring unit 4 therefore forms a structural unit. Within the monitoring unit 4, a signal generator 8, a splitter 10, a comparator 12 configured, in particular, as differential amplifier, a voltage meter 14 and an evaluating unit 16 are integrated. Additionally, an amplifier 18 and a coupling element 20, which is preferably formed as a directional coupler, are optionally integrated.

The measuring line 6 which is in particular formed as a spur line is connected to the monitoring unit 4, for example to a suitable terminal 21 such as, e.g., plug-in contact.

The measuring line 6 is in the illustrative embodiment of FIG. 1 a single-core line with one core, that is to say with one measuring conductor 24 surrounded by an insulation 22. Due to its design as a spur line, one end of the measuring line 6 is open and the measuring conductor 24 is therefore not electrically contacted.

The signal generator 8 generates a periodic alternating-voltage signal S, particularly a sinusoidal signal. This is divided in the splitter 10 into a reference signal R and into an operating signal LS. The operating signal LS is subsequently fed into the measuring conductor 24. In the illustrative embodiment, an internal conductor path is formed within the monitoring unit 4 which is led from the splitter 10 via the coupling element 20 to the terminal at which the measuring conductor 24 is connected.

The operating signal LS is reflected at the open end of the measuring line 6 because of the design as a spur line. The reflected component is propagated as return signal RS within the measuring conductor 24 in the opposite direction to the operating signal LS. The return signal RS is coupled via the coupling element 20 into a return conductor 26 within the monitoring unit 4. The return signal RS then coupled in is amplified via the optional amplifier 18 and supplied to a first input of the comparator 12. The reference signal R is present at a second input of the comparator 12. The comparator 12 generates a resultant signal S by summing or differentiating. The amplitude thereof is detected via the voltage meter 14 and supplied to the evaluating unit 16 as voltage measuring signal.

Figure 2:
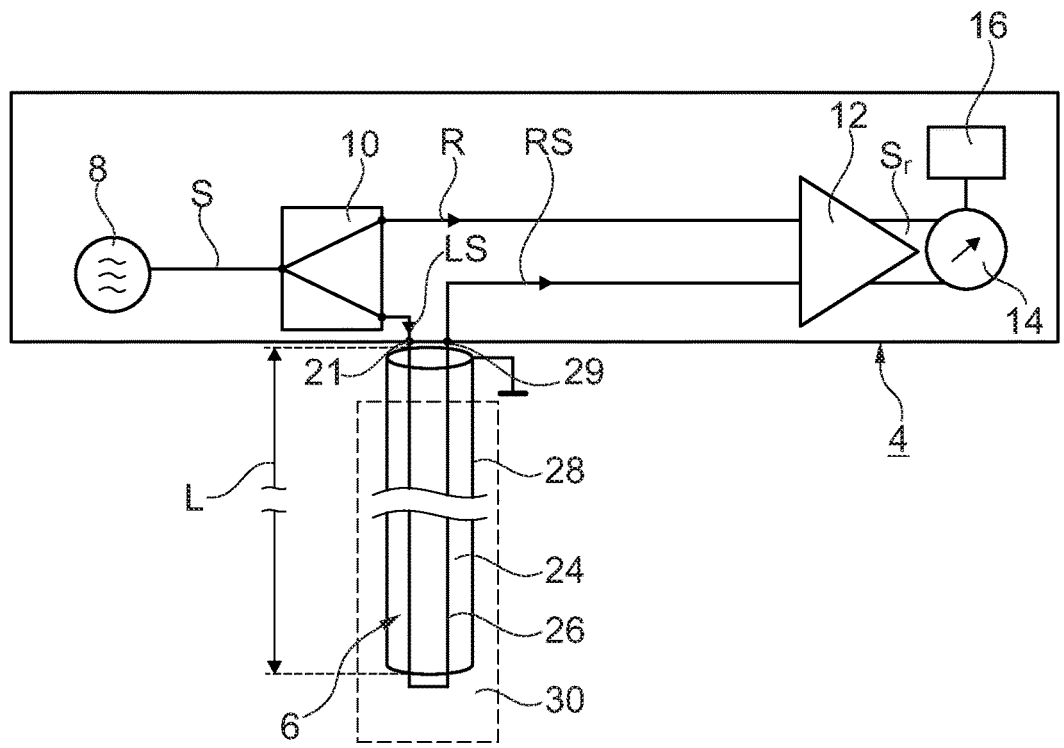
FIG. 2 is a schematic diagram of a second variant of the embodiment of the measuring arrangement.

In the variant of the embodiment according to FIG. 2, the measuring line 6 is replaced by a two-core line provided, in particular, with a shielding 28. The conductors of the two cores are connected to one another in this case at their ends. The conductors of the two cores together form the measuring conductor 24.

In this arrangement, one core is connected to the terminal 21 of the monitoring unit 4. Thus, the operating signal LS is fed from the splitter 10 into this core. The other core is connected to a further terminal 29 of the monitoring unit 4 configured as an input and is connected to the first input of the comparator 12 within the monitoring unit 4 via a conductor path. The reference signal R, in turn, is present at the second input of the comparator 12. As also in the variant of the embodiment according to FIG. 1, the voltage (amplitude) of the resultant signal Sr is measured and provided to an evaluating unit 16 by the voltage meter 4. In the variant of the embodiment of FIG. 2 the amplifier 18 is omitted in the illustrative embodiment.

In this variant of the embodiment the return signal RS which is present at the first input of the comparator 12 is identical to the operating signal LS, i.e. the operating signal LS is virtually looped through the measuring line 6 via the two short-circuited conductors of the measuring line 6 and supplied as the return signal RS to the first input of the comparator 12.

Figure 3:
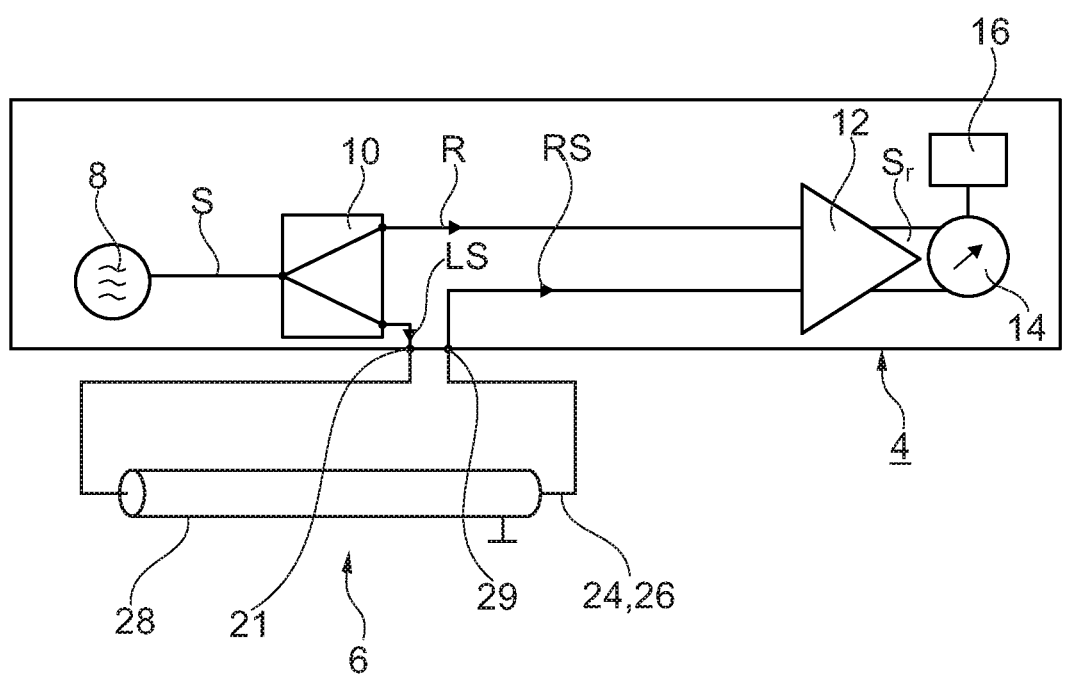
FIG. 3 is a schematic diagram of a third variant of the embodiment of the measuring arrangement.

FIG. 3, finally, shows a further, particularly simple variant of the embodiment in which a conductor of the measuring line 6 as measuring conductor 24, is connected, on the one hand, to a feed-in side on the side of the signal generator 8 and, on the other hand, to a receiver side on the side of the evaluating unit 16. In the illustrative embodiment, the measuring conductor 24 is connected to the two terminals 21, 29. The measuring line 6 is, for example, a coaxial line or also a two-wire line. In the coaxial line, one of the conductors (inner conductor, outer conductor) is the measuring conductor and the other one is preferably connected to reference potential (ground). In the case of the two-wire line, one of the conductors is also the measuring conductor 24 and the other preferably connected to reference potential.

The measuring arrangement 2 is particularly used for monitoring the measuring line 6 for a changed condition. This can be an external ambient condition or also an internal condition of the measuring line 6 itself. For this purpose, a state parameter, especially an ambient parameter, is monitored with the aid of the measuring arrangement. This state parameter is particularly the temperature.

In this context, the measuring principle is based on the fact that the propagation of the measuring signal coupled in within the measuring line 6 and thus a run time of the return signal RS also depends, among other things on the dielectric constant of the insulation 22. The dielectric constant is in turn temperature-dependent so that the run time of the return signal RS is temperature-dependent. The run time of the return signal RS is understood in this case to be the total time which the signal (operating signal LS plus return signal RS) needs for the path between the output of the splitter 10 up to the first input of the comparator 12.

Investigations have shown that, for example in the case of an ambient temperature of minus 40° C., the signal speed of the propagating signal is approximately 6 ns per meter and with an ambient temperature of 105° C. 8 ns per meter.

The measuring line 6 has a defined predetermined length L overall. This length in this case is traversed in both variants of the embodiment. If the length L is for example 10 m, then the run path for the signal is 20 m.

Assuming a maximum range of values to be monitored for the state parameter to be monitored, presently, for example, a maximum of about 145° for the temperature to be monitored (−40° C. to 105° C.), a difference in operating time between the minimum temperature and the maximum temperature of, for example, 40 ns is to be assumed overall with a line length L of 10 m. This corresponds to a maximum difference in operating time $\Delta t$ to be expected.

The signal paths for the reference signal R and the measuring signal (operating signal LS plus return signal RS) differ appropriately by the signal path via the measuring line 6. The signal paths within the monitoring unit for the reference signal R, on the one hand, and for the measuring signal, on the other hand, are therefore preferably identical. Overall, the signal paths for the reference signal R and the measuring signal are selected in such a manner that when the two signals are combined at defined normal conditions (e.g. at 20° Celsius), a defined predetermined phase shift of, for example, 90° or also 270° occurs at a "medium" run time of presently, for example, 7 ns.

Generally, the electrical signal path extended by the measuring line 6 leads to a defined shift in the phase angle of the return signal RS in comparison with the reference signal R. The amplitude of the resulting signal Sr changes, therefore, in dependence on the phase angle of the two signals R, RS with respect to one another. Since this depends on the temperature, in turn, it is possible to infer the temperature also directly from a phase change.

Especially in the case of a steady signal, particularly a sinusoidal signal, the two signal components are superimposed linearly at the inputs of the comparator. Overall, a change in voltage of the resultant signal Sr results which is at least essentially proportional to a temperature change.

To provide for an unambiguous evaluation, the frequency of the signal S generated is also selected in such a way that with the maximum difference in operating time $\Delta t$ to be expected, only a predetermined maximum phase offset occurs between the two signals. This maximum phase offset is preferably $\leq +/90°$ and preferably $\leq +/45°$.

In the above example, in which a maximum difference in operating time $\Delta t$ of 40 ns is to be expected and with a desired maximum phase shift of 90° (+/−45°), a duration of the period of 160 ns is thus obtained for a 360° period. From this, a frequency for the signal of about 6.25 MHz is obtained in the exemplary embodiment.

If the line length L is changed by a factor of 10 the frequency of the signal S to be fed in also changes by the factor 10, the frequency being reduced with increasing length L of the measuring line 6.

The measuring line 6 is led in this case within a component 30 to be monitored. This is, for example, a cable so that the temperature loading of the cable is thus measured and monitored. In dependence on this temperature monitoring a life span to be expected or the wear of the cable is suitably inferred.

In a second embodiment, the component 30 is a constructional unit to be monitored.

According to a third variant of the embodiment the measuring line 6 is embedded within a compound. The compound is, for example, concrete, i.e. the measuring line 6 is also concreted in. Via the entire measuring arrangement 2, a temperature can then be monitored during the setting of the concrete.

The invention claimed is:

1. A method for monitoring a line for changed ambient conditions, the line having a measuring line with a predetermined length and a measuring conductor surrounded by insulation, which comprises the steps of:

generating an analog signal being a periodic signal having a predetermined frequency;

dividing the analog signal into a reference signal and an operating signal;

feeding the operating signal into the measuring conductor;

combining a return signal obtained from the operating signal with the reference signal, wherein the return signal, under normal conditions, having a run time to be expected and under ambient conditions deviating from the normal conditions, a maximum run time difference to be expected and wherein a frequency is tuned to the maximum run time difference to be expected in such a manner that a phase shift is ≤180° by amount; and determining a measure for a changed condition by means of a phase shift between the reference signal and the return signal.

2. The method according to claim 1, which further comprises amplifying the return signal in such a manner that the return signal has a same amplitude as the reference signal.

3. The method according to claim 1, wherein the return signal is a reflected component of the operating signal and the measuring line is a spur line.

4. The method according to claim 1, which further comprises coupling the return signal into a return conductor separate from the measuring conductor.

5. The method according to claim 1, which further comprises forming the analog signal as a sinusoidal signal having a predetermined frequency.

6. The method according to claim 1, wherein the phase shift is ≤90°.

7. The method according to claim 1, wherein the phase shift is ≤45°.

8. A method for monitoring a line for changed ambient conditions, the line having a measuring line with a predetermined length and a measuring conductor surrounded by insulation, which comprises the steps of:

generating an analog signal being a periodic signal having a predetermined frequency;

dividing the analog signal into a reference signal and an operating signal;

feeding the operating signal into the measuring conductor;

combining a return signal obtained from the operating signal with the reference signal, wherein the return signal, under normal conditions, having a run time to be expected and under ambient conditions deviating from the normal conditions, a maximum run time difference to be expected and wherein a frequency is tuned to the maximum run time difference to be expected in such a manner that a phase shift is ≤180° by amount; and superimposing the reference signal and the return signal to form a resultant signal and from an amplitude of the resultant signal, a measure is determined for a changed condition.

* * * * *